United States Patent
Qi et al.

(10) Patent No.: US 12,360,075 B1
(45) Date of Patent: Jul. 15, 2025

(54) CONSTRUCTION METHOD AND APPLICATION OF microRNA ELECTROCHEMICAL BIOSENSOR

(71) Applicant: Xuzhou Central Hospital, Xuzhou (CN)

(72) Inventors: Yujuan Qi, Xuzhou (CN); Zhao Liu, Xuzhou (CN); Sen Zheng, Xuzhou (CN); Zhenbei Li, Xuzhou (CN); Juan Gu, Xuzhou (CN); Fangfang Hu, Xuzhou (CN); Yijuan Cao, Xuzhou (CN); Qingqing Sun, Xuzhou (CN); Xiaoyan Liu, Xuzhou (CN); Nan Jiang, Xuzhou (CN)

(73) Assignee: Xuzhou Central Hospital, Xuzhou (CN)

( * ) Notice: Subject to any disclaimer, the term of this patent is extended or adjusted under 35 U.S.C. 154(b) by 0 days.

(21) Appl. No.: 18/941,885

(22) Filed: Nov. 8, 2024

(30) Foreign Application Priority Data

Jun. 24, 2024 (CN) .......................... 202410814570.8

(51) Int. Cl.
  *G01N 27/327* (2006.01)
  *C12Q 1/6825* (2018.01)
  *C12Q 1/6876* (2018.01)

(52) U.S. Cl.
  CPC ....... *G01N 27/3277* (2013.01); *C12Q 1/6825* (2013.01); *C12Q 1/6876* (2013.01); *G01N 27/3278* (2013.01); *C12Q 2600/178* (2013.01)

(58) Field of Classification Search
  CPC ........... G01N 27/3277; G01N 27/3278; C12Q 1/6825; C12Q 1/6876; C12Q 2600/178; C12Q 2521/345; C12N 15/113; C12N 2310/127
  See application file for complete search history.

(56) References Cited

U.S. PATENT DOCUMENTS

2019/0048402 A1* 2/2019 Pingarrón ............ C12Q 1/6804

FOREIGN PATENT DOCUMENTS

| CN | 108663354 A | 10/2018 |
|---|---|---|
| CN | 111440851 A | 7/2020 |
| CN | 116359305 A | 6/2023 |
| CN | 117929498 A | 4/2024 |

OTHER PUBLICATIONS

Qi et al. Construction of an efficient microRNA sensing platform based on terminal deoxynucleotidyl transferase-mediated synthesis of copper nanoclusters. Sensors and Actuators: B. Chemical 2025; 424: 136892. (Year: 2025).*

Huang et al. Recent Advances on DNAzyme-Based Sensing. Chem. Asian J. 2022; 17: e202101414 (Year: 2022).*

(Continued)

*Primary Examiner* — Angela M. Bertagna
(74) *Attorney, Agent, or Firm* — Pilloff Passino & Cosenza LLP; Rachel K. Pilloff; Sean A. Passino

(57) ABSTRACT

A construction method and an application of a miRNA electrochemical biosensor are provided. The construction method includes the following steps: fixing a SP substrate chain to a surface of AuNPs/GCE electrode, and performing sealing treatment with mercaptohexanol to obtain a miRNA electrochemical biosensor; a nucleotide sequence of the SP substrate chain is shown in SEQ ID NO:1, a 5' end of the nucleotide sequence is modified with SH—$(CH_2)_6$—, and a ninth base of the nucleotide sequence is an rA cleavage site.

6 Claims, 9 Drawing Sheets

Specification includes a Sequence Listing.

(56) References Cited

OTHER PUBLICATIONS

Mahdiannasser, M. and Karami, Z. An innovative paradigm of methods in microRNAs detection: highlighting DNAzymes, the illuminators. Biosensors and Bioelectronics 2018; 107: 123-144 (Year: 2018).*

Li et al. Sensitive and point-of-care detection of lead ion in river water mediated by terminal deoxynucleotidyl transferase. Sensors and Actuators: B. Chemical 2024; 401: 134909 (Year: 2024).*

Li et al. Label-free detection of miRNA cancer markers based on terminal deoxynucleotidyl transferase-induced copper nanoclusters. Analytical Biochemistry 2019; 585: 113346 (Year: 2019).*

Zhang Li, et al., Hybridization Chain Reaction-Mediated Luminescent Silver Nanocluster System for Amplified Detection of miRNA-21, Chinese Journal of Analytical Chemistry, Sep. 30, 2020, vol. 48(9), pp. 1193-1201. (abstract at end translated) doi: 10.19756/j.issn.0253-3820.201144 Claims involved: 1-7.

Notification to Grant Patent Right for Invention dated Aug. 28, 2024, in SIPO application No. 202410814570.8.

Retrieval report dated Jul. 19, 2024, in SIPO application No. 202410814570.8.

\* cited by examiner

SEQUENCE LISTING

```
Sequence total quantity: 6
SEQ ID NO: 1            moltype = DNA  length = 17
FEATURE                 Location/Qualifiers
source                  1..17
                        mol_type = other DNA
                        organism = synthetic construct
SEQUENCE: 1
gtcactatag aaagatg                                                 17

SEQ ID NO: 2            moltype = DNA  length = 41
FEATURE                 Location/Qualifiers
source                  1..41
                        mol_type = other DNA
                        organism = synthetic construct
SEQUENCE: 2
gactagcatg aagagagggt caacatcagt ctgataagct a                      41

SEQ ID NO: 3            moltype = DNA  length = 36
FEATURE                 Location/Qualifiers
source                  1..36
                        mol_type = other DNA
                        organism = synthetic construct
SEQUENCE: 3
atcagactga tgttgaccct cggtcgaaat agtgac                            36

SEQ ID NO: 4            moltype = DNA  length = 30
FEATURE                 Location/Qualifiers
source                  1..30
                        mol_type = other DNA
                        organism = synthetic construct
SEQUENCE: 4
catcttcttc cgagcctctt catgctagtc                                   30

SEQ ID NO: 5            moltype = DNA  length = 35
FEATURE                 Location/Qualifiers
source                  1..35
                        mol_type = other DNA
                        organism = synthetic construct
SEQUENCE: 5
atcagactga tgttgaccct ctcttcatgc tagtc                             35
```

```
SEQ ID NO: 6            moltype = RNA   length = 22
FEATURE                 Location/Qualifiers
source                  1..22
                        mol_type = other RNA
                        organism = synthetic construct
SEQUENCE: 6
tagcttatca gactgatgtt ga                                               22
```

CONSTRUCTION METHOD AND APPLICATION OF microRNA ELECTROCHEMICAL BIOSENSOR

CROSS-REFERENCE TO RELATED APPLICATIONS

This application claims priority to Chinese Patent Application No. 202410814570.8, filed on Jun. 24, 2024, the contents of which are hereby incorporated by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: PPH-US-2024-13936 Sequence.xml
Creation date: 1 Nov. 2024
Byte size: 6,155

TECHNICAL FIELD

The present disclosure relates to the technical field of biosensors, and in particular to a construction method and an application of a micro ribonucleic acid (miRNA) electrochemical biosensor.

BACKGROUND

Endogenous, non-coding miRNAs are important in regulating human gene expression and may serve as effective biomarkers in the preventive, developmental and therapeutic stages of disease. Studies have shown that miRNA 21 is expressed at high levels in cancers such as breast, cervical, and lung adenocarcinomas, and therefore monitoring changes in the level of miRNA 21 may reflect the disease status of the organism. Currently, common techniques for miRNA detection include fluorescence, surface-enhanced Raman spectroscopy (SERS), surface plasmon resonance (SPR), colorimetric analysis and electrochemical techniques, with electrochemical techniques being favored by researchers because of their advantages of high sensitivity, fast detection speed, low analytical cost, and ease of miniaturization. To achieve sensitive detection of miRNAs, scientists usually employ electrochemical markers to enhance the signal output. With excellent conductive and catalytic properties, large specific surface area and high loading capacity, nanomaterials are widely used as electrochemical markers. However, most of the methods usually require pre-labelling of electrochemical signals using chemical modification operations, which increases the cost of detection and complexity of operation. Therefore, label-free and efficient electrochemical sensing methods are urgently required.

SUMMARY

The present disclosure aims to provide a construction method and an application of a miRNA electrochemical biosensor, so as to solve the problems existing in the prior art. The miRNA electrochemical biosensor provided by the present disclosure is highly sensitive and easy to operate, which enables sensitive detection of miRNA 21 in cancer cell samples without pre-labelling the electrochemical signals, and has important application value in the fields of clinical diagnosis and drug research of cervical cancer and breast cancer.

Metal nanoclusters have excellent electrical conductivity, optical properties, quantum effects and surface atomic activity compared to bulk materials. An ideal template for the synthesis of metal nanoclusters is deoxyribonucleic acid (DNA), given the strong affinity between metal ions and DNA. The metal ions are attached to the nitrogen or phosphate oxygens of aromatic bases, which are immobilized by the polyanionic backbone through electrostatic forces, preventing excessive adsorption and nucleation of the metal precursors, thus synthesizing highly dispersed nanoparticles. DNA templates have received much attention in the field of bioanalysis as they provide a good combination of the properties of metal nanoclusters and DNA amplification strategies. In a previous study, by using cytosine-rich DNA strands as templates, silver nanoclusters (AgNCs) are synthesized in-situ on a sensing electrode, enabling sensitive detection of different biomarkers and multiple logic gates analysis. Due to the high dependence of metal nanoclusters on the length and number of DNA templates, the DNA templates used in these systems are relatively short and of fixed sequence, with limited signal amplification capability and detection efficiency. In order to solve this problem, the present disclosure constructs a miRNA electrochemical biosensor based on terminal transferase to regulate the signal output of copper nanoclusters, and the miRNA electrochemical biosensor may use terminal transferase to regulate the growth of DNA templates and synthesize metal nanoclusters in situ to achieve efficient signal output and detection.

Based on this, the present disclosure provides the following technical schemes.

The present disclosure provides a construction method of a miRNA electrochemical biosensor, including steps of fixing an SP substrate chain to a surface of an AuNPs/GCE electrode, and performing sealing treatment with mercaptohexanol to obtain the miRNA electrochemical biosensor; and a nucleotide sequence of the SP substrate chain is shown in SEQ ID NO:1, a 5' end of the nucleotide sequence is modified with SH—$(CH_2)_6$—, and a ninth base of the nucleotide sequence is an rA cleavage site.

Optionally, the AuNPs/GCE electrode is prepared by an electrochemical deposition method.

Optionally, the electrochemical deposition method includes steps of depositing a layer of choline chloride on a surface of a glass carbon electrode (GCE), and then placing in a $HAuCl_4$ solution for cyclic voltammetric deposition to obtain the AuNPs/GCE electrode.

Optionally, a method for fixing the SP substrate chain to the surface of the AuNPs/GCE electrode includes following steps: firstly, reacting the SP substrate chain with tris(2-carboxyethyl) phosphine to obtain a reaction solution, and then dropping the reaction solution on the surface of the AuNPs/GCE electrode for light-proof reaction.

The present disclosure also provides a miRNA electrochemical biosensor constructed according to the construction method.

The present disclosure also provides an application of the miRNA electrochemical biosensor in preparing a miRNA 21 detection kit based on terminal transferase modulation of copper nanocluster signaling output.

The present disclosure also provides a miRNA 21 detection kit based on terminal transferase modulation of copper nanocluster signaling output, which includes AP1/DP1-DP2 double-strand, an AP2 probe and the miRNA electrochemical biosensor;

the AP1/DP1-DP2 double strand is obtained by hybridization reaction of an auxiliary probe AP1, a DNAzyme probe DP1 and a DNAzyme probe DP2;

a nucleotide sequence of the auxiliary probe AP1 is shown in SEQ ID NO:2;

a nucleotide sequence of the DNAzyme probe DP1 is shown in SEQ ID NO:3;

a nucleotide sequence of the DNAzyme probe DP2 is shown in SEQ ID NO:4; and a nucleotide sequence of the AP2 probe is shown in SEQ ID NO:5.

Optionally, reaction conditions of the hybridization reaction include heating at 95 degrees Celsius (° C.) for 5 minutes (min), and then cooling to 25° C. at a rate of 1° C./min.

Optionally, the miRNA 21 detection kit further includes copper sulfate and a reducing agent.

Optionally, the reducing agent is ascorbic acid.

The present disclosure achieves the following technical effects.

The present disclosure constructs a miRNA electrochemical biosensor based on terminal transferase modulation of copper nanocluster signaling output. This miRNA electrochemical biosensor enables cyclic amplification of miRNAs using the toehold chain substitution reaction, and in situ synthesis and signal output of copper nanoclusters using the polymerization product of end-transferase as a template, which then allows for the sensitive detection of miRNA 21 in cancer cell samples.

The miRNA electrochemical biosensor provided by the present invention is highly sensitive and easy to operate, which enables sensitive detection of miRNA 21 in cancer cell samples without pre-labelling the electrochemical signals, and has important application value in the fields of clinical diagnosis and drug research of cervical cancer and breast cancer.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings described below are only some embodiments of the present disclosure, and other drawings can be obtained according to these drawings without creative work for ordinary people in the field.

DETAILED DESCRIPTION OF THE EMBODIMENTS

A number of exemplary embodiments of the present disclosure will now be described in detail, and this detailed description should not be considered as a limitation of the present disclosure, but should be understood as a more detailed description of certain aspects, characteristics and embodiments of the present disclosure.

It should be understood that the terminology described in the present disclosure is only for describing specific embodiments and is not used to limit the present disclosure. In addition, for the numerical range in the present disclosure, it should be understood that each intermediate value between the upper limit and the lower limit of the range is also specifically disclosed. Intermediate values within any stated value or stated range, as well as each smaller range between any other stated value or intermediate values within the stated range are also included in the present disclosure. The upper and lower limits of these smaller ranges can be independently included or excluded from the range.

Unless otherwise specified, all technical and scientific terms used herein have the same meaning as commonly understood by one of ordinary skill in the art to which this present disclosure relates. Although the present disclosure only describes the preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present disclosure without departing from the scope or spirit of the present disclosure. Other embodiments will be apparent to the skilled person from the description of the present disclosure. The description and embodiments of that present disclosure are exemplary only.

The terms "including", "comprising", "having" and "containing" used in this specification are all open terms, which means including but not limited to.

Figure 1:
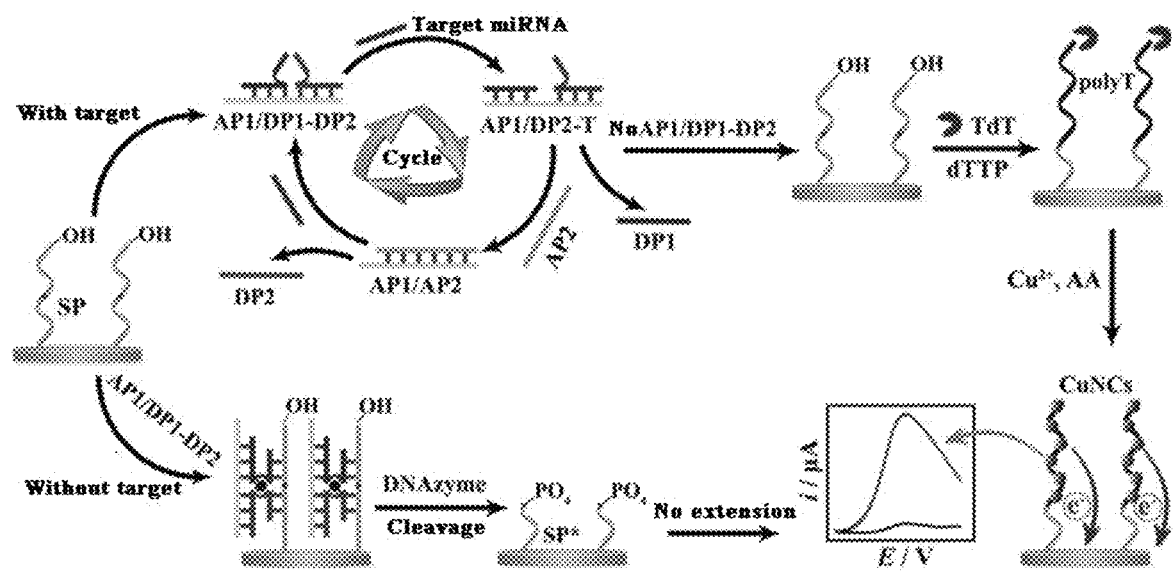
FIG. 1 is a schematic diagram of a miRNA electrochemical biosensor according to the present disclosure.

The present disclosure constructs a miRNA electrochemical biosensor based on terminal transferase to regulate the signal output of copper nanoclusters, and fixes SP substrate chain and mercaptohexanol MCH to the surface of AuNPs/GCE electrode to obtain a sensing interface MCH/SP/AuNPs/GCE (FIG. 1). Among them, SP substrate chain contains rA cleavage site, and DNAzyme probes DP1 and DP2 contain partial catalytic sequences. When the double-stranded structure of AP1/DP1-DP2 is formed, the two strands of DP1 and DP2 are close to each other to form an activated DNAzyme, and the SP strand is cut into two fragments at the rA site. The short-chain SP* with 5' phosphate terminal generated on the electrode surface is not applicable for the amplification of terminal transferase TdT.

When the target miRNA 21 is added, miRNA 21 firstly carries out the chain displacement reaction through the toehold at the end of AP1 chain, so that DP1 is replaced from the double-stranded structure, and at the same time, a new toehold is exposed in the middle of AP1 chain. AP2 takes this toehold as a foothold to carry out the second-step chain replacement reaction, replacing miRNA 21 and DP2, and realizing the recycling of miRNA 21. After many cycles, the structure of AP1/DP1-DP2 is destroyed, and a large number of AP1/AP2 double strands are generated. At this time, the activity of DNAzyme is inhibited, and the SP chain shows 3' hydroxyl end. TdT catalyzes the binding of free deoxythymidine triphosphate dTTP to SP chain, producing a large number of repeated T sequences (polyT). The polyT may bind copper ions to generate copper nanoclusters under the reduction of ascorbic acid, and then the sensitive detection of miRNA 21 may be realized by detecting the stripping voltammetric signal of copper. The details are as follows.

Embodiment 1

Figure 6:
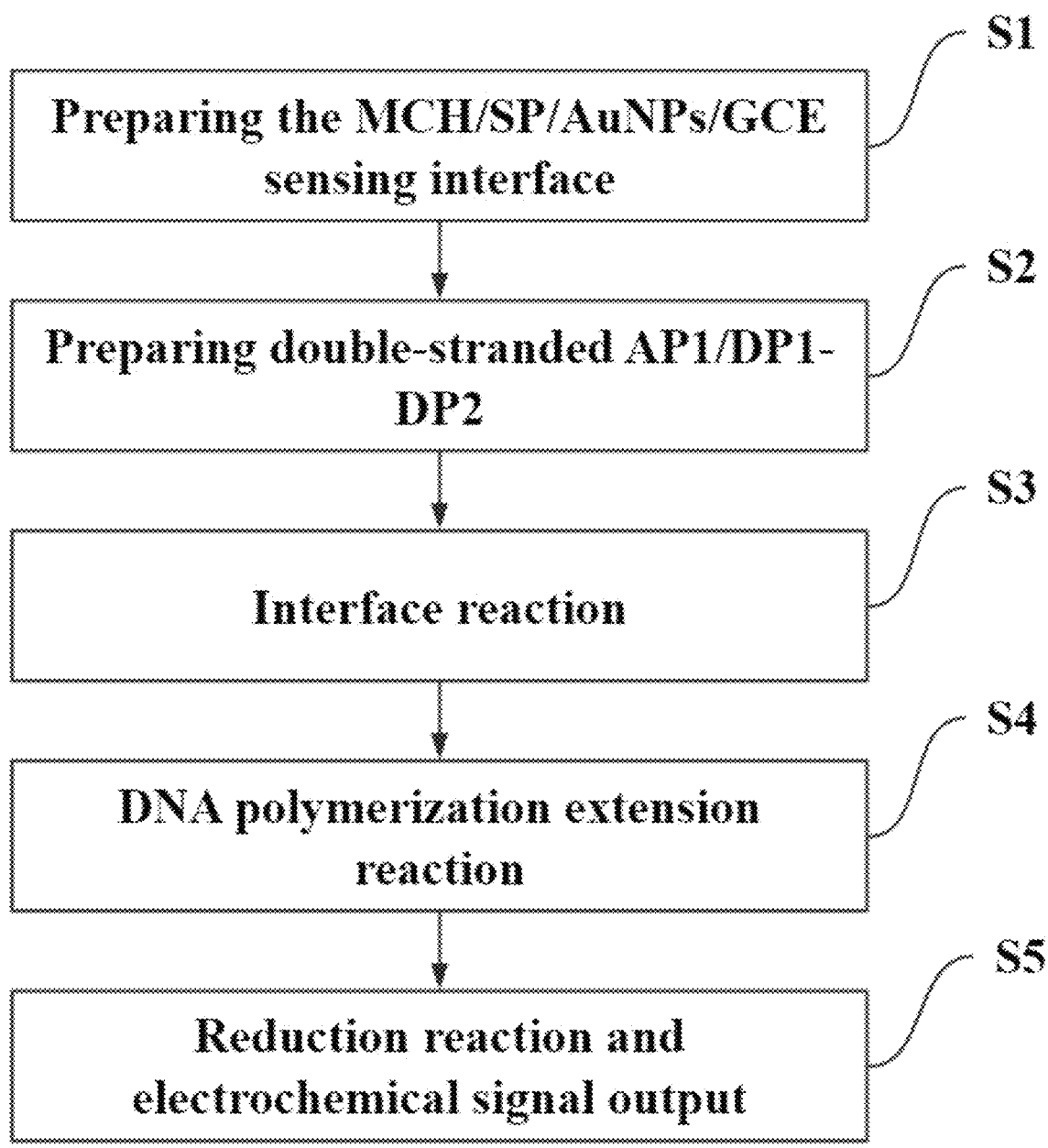
FIG. 6 is a process illustrating the construction method of the miRNA electrochemical biosensor provided by the present disclosure.

The construction method of the miRNA electrochemical biosensor includes the following step as shown in FIG. 6:
S1: preparing the MCH/SP/AuNPs/GCE sensing interface:
AuNPs/GCE electrode is prepared by electrochemical deposition, then SP substrate chain is fixed to the surface of AuNPs/GCE, and MCH/SP/AuNPs/GCE is sealed with mercaptohexanol. The specific operation is as follows: firstly, a layer of choline chloride is deposited on the surface of glass carbon electrode (GCE), and then it is placed in $HAuCl_4$ solution for cyclic voltammetry deposition to obtain AuNPs/GCE; then, the SP substrate chain reacts with tris(2-carboxyethyl) phosphine for 1 hour (h) to obtain a reaction solution, and the reaction solution is dripped on the surface of AuNPs/GCE to react in the dark for 8 h, and then mercaptohexanol (MCH) is dripped on the electrode for sealing for 2 h after washing, so that the sensing interface of MCH/SP/AuNPs/GCE is obtained;
among them, the sequence of SP substrate chain is 5'-SH—$(CH_2)_6$-GTCACTAT/rA/GAAAGATG-3'(SEQ ID NO:1).
S2: preparing double-stranded AP1/DP1-DP2:
the auxiliary probe AP1 is mixed with DNAzyme probes DP1 and DP2, heated at 95° C. for 5 min, and then cooled to 25° C. at the rate of 1° C./min to obtain the double-stranded AP1/DP1-DP2;
among them, the sequence of AP1 is 5'-GACTAGCATGAAGAGAGGGTCAACATCAGTCTGA-TAAGCTA-3'(SEQ ID NO:2); the sequence of DP1 is 5'-ATCAGACT-GATGTTGACCCTCGGTCGAAATAGTGAC-3' (SEQ ID NO:3); and the sequence of DP2 is 5'-CATCTTCTTCCGAGCCTCTTCATGCTAGTC-3' (SEQ ID NO:4);
S3: interface reaction:
double-stranded probes AP1/DP1-DP2 and AP2 are mixed with miRNA 21 with different concentrations (0 attomolar (aM), 100 aM, 1 femtomolar (fM), 10 fM, 100 fM, 1 picomole (pM) and 10 pM) (the molar ratio of probes AP1/DP1-DP2 to AP2 is 1:1) and dripped into MCH/SP/AuNPs of the sensing electrode. and the reaction is carried out for 80 min.
Among them, the sequence of AP2 probe is 5'-ATCA-GACTGATGTTGACCCTCTCTTCATGCTAGTC-3' (SEQ ID NO:5); the sequence of miRNA 21 is 5'-UAGC-UUAUCAGACUGAUGUUGA-3'(SEQ ID NO:6);
S4: DNA polymerization extension reaction:
after the interface reaction in step S3 is completed, the sensor electrode is cleaned, and a mixed solution containing 5 U terminal transferase (TdT) and 1 millimolar (mM) deoxythymidine triphosphate (dTTP) is added, and the DNA polymerization extension reaction is carried out at 37° C. for 50 min.
S5: reduction reaction and electrochemical signal output:
after the DNA polymerization extension reaction in step S4 is completed, the sensor electrode is incubated with 1 mM copper sulfate for 20 min, and then washed and reduced with 100 micromolar (pM) ascorbic acid for 0.5 h to obtain copper nanoclusters; finally, in the potential window of 0 to 0.5 V, differential pulse stripping voltammetry (DPSV) is used to realize the electrochemical signal output of miRNA 21.

Effect Verification

1. Verification of the Construction of MCH/SP/AuNPs/GCE Sensor Interface

Figure 2A:
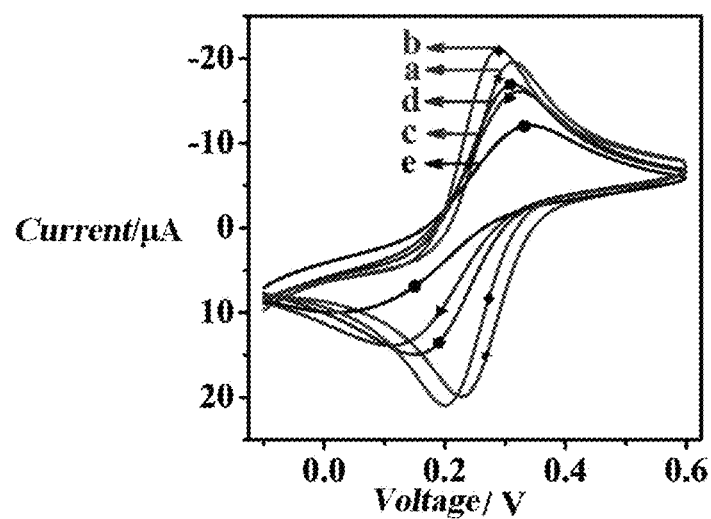
FIG. 2A is a cyclic voltametric response diagram of the sensing interface in the miRNA electrochemical biosensor of the present disclosure.
Figure 2B:
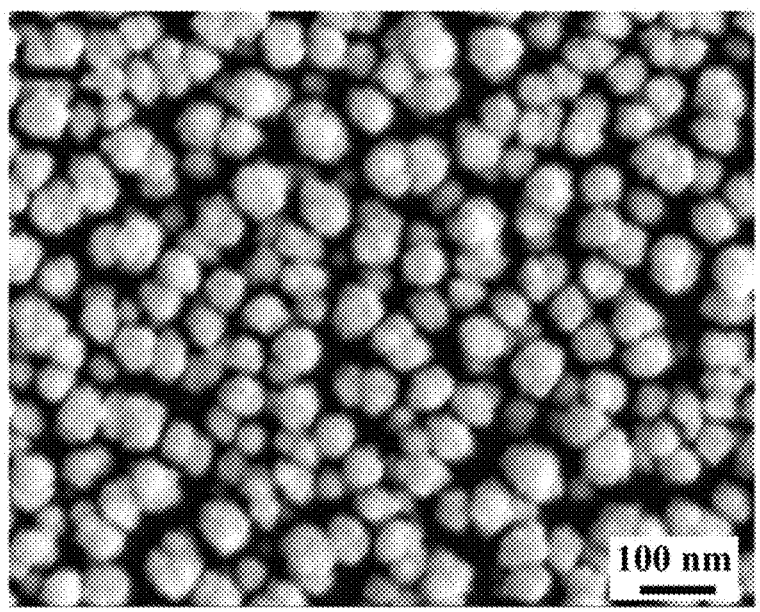
FIG. 2B is a scanning electron microscope (SEM) image of AuNPs/GCE.

In order to verify the construction of MCH/SP/AuNPs/GCE sensing interface, the current response of $[Fe(CN)6]^{3-/4-}$ on different interfaces is characterized by cyclic voltammetry technology. As shown in FIG. 2A, compared with the bare glass carbon electrode (GCE) (curve a), the current signal of gold nanoparticles (AuNPs) after deposition is obviously enhanced (curve b), indicating that AuNPs has excellent conductivity. After the SP substrate chain is immobilized, the negative charge of SP phosphate skeleton and $[Fe(CN)6]^{3-/4-}$ probe have electrostatic repulsion, which reduces the current (curve c). After further sealing the electrode with mercaptohexanol MCH, the current signal is recovered slightly (curve d). In contrast, after the addition of miRNA 21, AP1/DP1-DP2, AP2, TdT, and dTTP reactions, the current signal decreases significantly (curve e), suggesting that miRNA 21 triggers the DNA elongation reaction. From the SEM characterization in FIG. 2B, it is evident that the AuNPs are uniformly dispersed on the electrode surface and the average diameter of the nanoparticles is about 75 nm.

2. Feasibility Verification of Detection Method

Figure 3A:
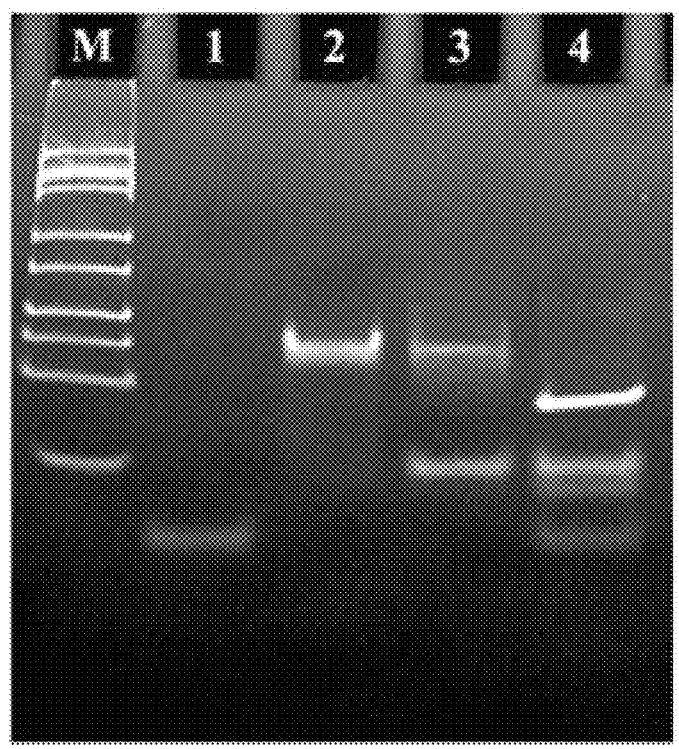
FIG. 3A is a characterization diagram of toehold chain displacement reaction.

In order to prove the feasibility of the detection method in the present disclosure, the present disclosure carries out polyacrylamide gel electrophoresis test. As shown in FIG. 3A, the AP1/DP1-DP2 band shows a lower migration rate (lane 2) compared with the miRNA 21 band (lane 1). After the mixed reaction of AP1/DP1-DP2 and miRNA 21, two different bands (lane 3) are obtained, in which the upper band corresponds to the AP1/DP2-miRNA 21 double-stranded complex, and the other band has higher electrophoretic mobility and corresponds to the DP1 chain released by the chain displacement reaction. After AP2 is added (lane 4), miRNA 21 band appeares, and a new band with low electrophoretic mobility is obtained, which is derived from the reaction product AP1/AP2. This phenomenon indicates that the design of toehold chain displacement reaction is successful.

Figure 3B:
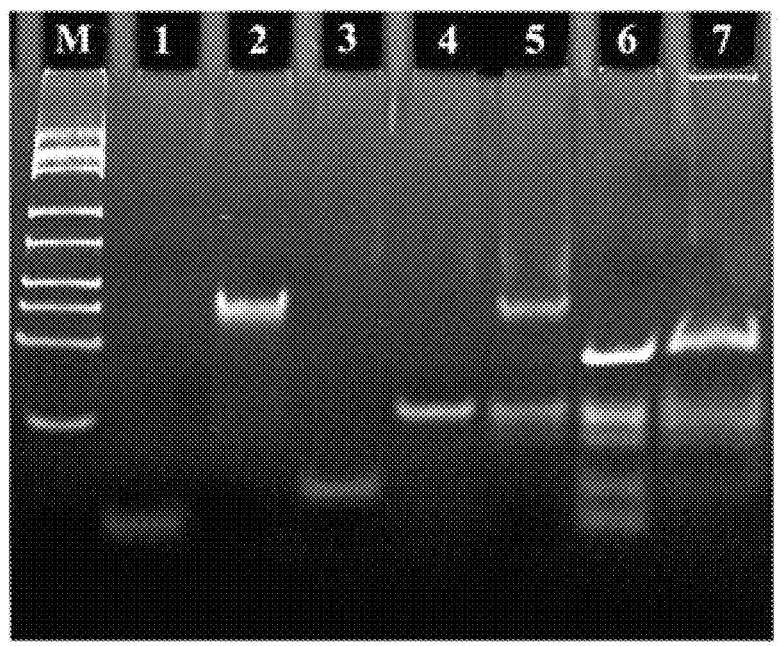
FIG. 3B is a characterization diagram of DNA polymerization extension reaction.

The present disclosure further studies the feasibility of DNA extension reaction mediated by TdT. As may be seen from FIG. 3B, SP, AP1/DP1-DP2, miRNA 21 and AP2 show clear bands in lanes 1 to 4 respectively. After reacting SP, AP1/DP1-DP2 with AP2, the SP band disappears (lane 5), indicating that AP1/DP1-DP2 has undergone DNAzyme shearing. However, in the presence of miRNA 21, the bands of SP chain are clearly visible (lane 6), which indicates that the shearing activity of DNAzyme is inhibited by the chain replacement reaction. After further incubation with TdT and dTTP, a new band with low mobility is appeared above lane 7, which corresponds to the electrophoresis signal of polyT sequence, indicating that the DNA extension reaction mediated by TdT is feasible.

3. Sensitivity Detection

Figure 4A:
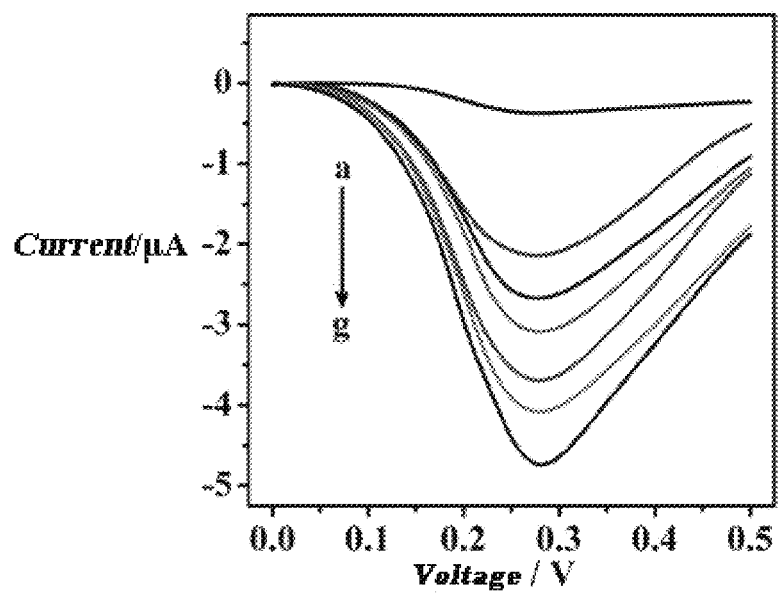
FIG. 4A shows the differential pulse stripping voltammetry (DPSV) response caused by different concentrations of miRNA 21.
Figure 4B:
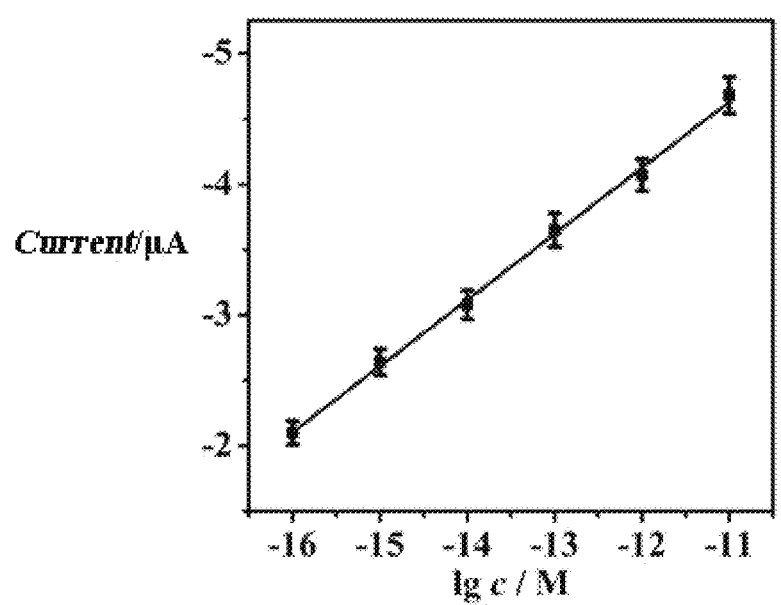
FIG. 4B is a linear diagram of the quantitative detection diagram of miRNA21 of the miRNA electrochemical biosensor of the present disclosure.

The current response caused by different concentrations of miRNA 21 is recorded by DPSV to study the sensitivity of the sensing system. As may be seen from FIG. 4A, the DPSV response signal increases with the increase of the concentration of miRNA 21. As shown in FIG. 4B, there is a good linear relationship ($R^2=0.9979$) between the current value and the logarithmic value of miRNA 21 concentration in the range of 100 aM to 10 pM, and the linear regression equation is i=0.5050 $\lg c_{miRNA\ 21}$+10.19. According to the calculation formula LOD=$3S_b$/m, the detection limit (LOD) is 36 aM, where $S_b$ is the standard deviation of the blank response and m is the slope of the calibration curve.

The above experimental results show that the sensor may quantitatively detect miRNA 21, and the detection limit is better than a large number of reported sensors.

4. Detection of Cancer Cell Samples

In order to investigate the applicability of the sensor, the sensor of Embodiment 1 is further applied to the detection of samples of cervical cancer cell Hela and breast cancer cell MCF-7.

The detection method is the same as that of Embodiment 1, except that miRNA 21 is replaced by the sample solution of cervical cancer cell Hela or breast cancer cell MCF-7, and the current response of the sensor to different numbers of cells (0, 100, 1000 and 10000) is detected. The detection results are shown in FIG. 5.

Figure 5:
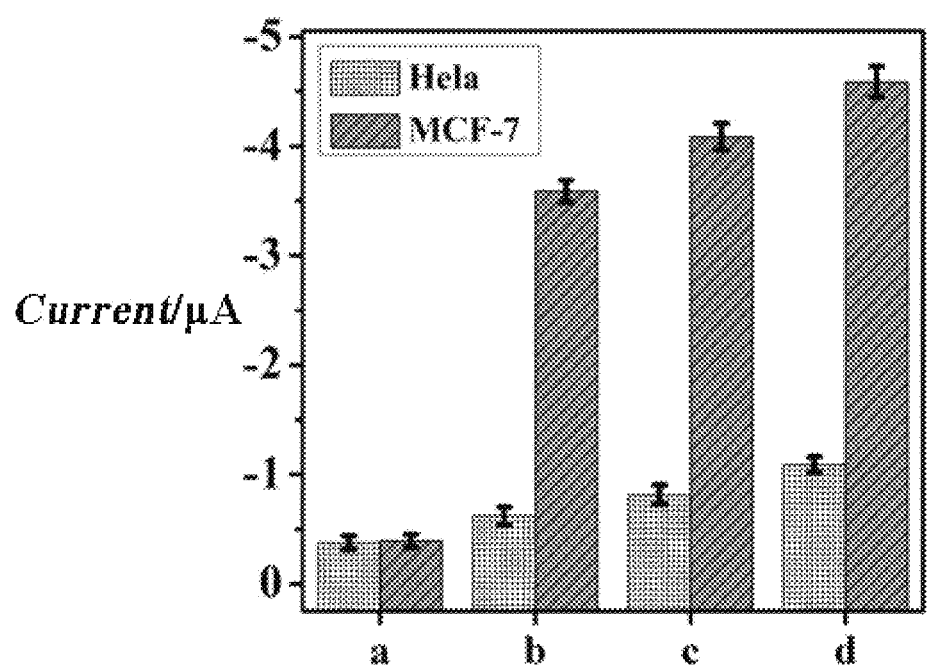
FIG. 5 is a statistical diagram of the detection results of cancer cell samples detected by the miRNA electrochemical biosensor of the present disclosure.

As observed from FIG. 5, compared with the blank buffer (column A), the cell lysates of Hela and MCF-7 increase the current of the sensor (columns b-d), and the current signal increases with the increase of cell number. It is worth noting that compared with MCF-7 cells, even if the number of Hela cells is increased to 10000, the DPSV current caused by HeLa cells is only slightly increased. This shows that miRNA 21 has a high expression level in MCF-7 cells, but low expression in Hela cells, which is consistent with previous reports.

5. Recovery Experiment with Standard Addition

According to the present disclosure, miRNA 21 with different contents (100 aM, 10 fM and 1000 fM) is added to a serum sample, and a standard addition recovery experiment is carried out. The experimental results show that the recovery rate is between 97.6% and 105.1%, and the relative standard deviation is between 2.7% and 4.8%, which shows that the sensing platform may detect miRNA 21 in complex biological samples.

The above-mentioned embodiments only describe the preferred mode of the present disclosure, and do not limit the scope of the present disclosure. Under the premise of not departing from the design spirit of the present disclosure, various modifications and improvements made by ordinary technicians in the field to the technical scheme of the present disclosure shall fall within the protection scope determined by the claims of the present disclosure.

What is claimed is:

1. A miRNA 21 detection kit for use in a method comprising terminal transferase modulation of copper nanocluster signaling output, comprising an AP1/DP1-DP2 double strand, an AP2 probe and a miRNA electrochemical biosensor; wherein
the AP1/DP1-DP2 double strand is obtained by hybridization of an auxiliary probe AP1, a DNAzyme probe DP1 and a DNAzyme probe DP2;
the nucleotide sequence of the auxiliary probe AP1 is shown in SEQ ID NO:2;
the nucleotide sequence of the DNAzyme probe DP1 is shown in SEQ ID NO:3;
the nucleotide sequence of the DNAzyme probe DP2 is shown in SEQ ID NO:4; and
the nucleotide sequence of the AP2 probe is shown in SEQ ID NO:5;
the miRNA electrochemical biosensor is constructed by a method comprising steps of fixing an SP substrate chain to a surface of an AuNPs/GCE electrode, and performing sealing treatment with mercaptohexanol to obtain the miRNA electrochemical biosensor; and
the nucleotide sequence of the SP substrate chain is shown in SEQ ID NO:1, and the 5' end of the nucleotide sequence of the SP substrate chain is modified with SH—$(CH_2)_6$, and the ninth base of the nucleotide sequence of the SP substrate chain is an rA cleavage site.

2. The miRNA 21 detection kit according to claim 1, wherein the AuNPs/GCE electrode is prepared by an electrochemical deposition method.

3. The miRNA 21 detection kit according to claim 2, wherein the electrochemical deposition method comprises steps of firstly depositing a layer of choline chloride on a surface of a glass carbon electrode (GCE), and then placing the GCE in a $HAuCl_4$ solution for cyclic voltammetric deposition to obtain the AuNPs/GCE electrode.

4. The miRNA 21 detection kit according to claim 1, wherein the method for fixing the SP substrate chain to the surface of the AuNPs/GCE electrode comprises: firstly, reacting the SP substrate chain with tris(2-carboxyethyl) phosphine to obtain a reaction solution, and then dropping the reaction solution onto the surface of the AuNPs/GCE electrode to perform a light-proof reaction.

5. The miRNA 21 detection kit according to claim 1, wherein the miRNA 21 detection kit further comprises copper sulfate and a reducing agent.

6. The miRNA 21 detection kit according to claim 5, wherein the reducing agent is ascorbic acid.

* * * * *